(12) United States Patent  (10) Patent No.: US 7,963,768 B2
Hilliard  (45) Date of Patent: Jun. 21, 2011

(54) SELF-LIGATING ORTHODONTIC BRACKET ASSEMBLY

(76) Inventor: Jack Keith Hilliard, Lakeland, FL (US)

( * ) Notice: Subject to any disclaimer, the term of this patent is extended or adjusted under 35 U.S.C. 154(b) by 105 days.

(21) Appl. No.: 12/552,854

(22) Filed: Sep. 2, 2009

(65) Prior Publication Data

US 2010/0062387 A1    Mar. 11, 2010

Related U.S. Application Data

(60) Provisional application No. 61/094,511, filed on Sep. 5, 2008.

(51) Int. Cl.
*A61C 3/00* (2006.01)
(52) U.S. Cl. ............................. 433/11; 433/12
(58) Field of Classification Search .................. 433/2–24
See application file for complete search history.

(56) References Cited

U.S. PATENT DOCUMENTS

| | | | |
|---|---|---|---|
| 2,011,575 A | 8/1935 | Ford | |
| 3,504,438 A | 4/1970 | Wittman et al. | |
| 3,772,787 A | 11/1973 | Hanson | |
| 4,144,642 A | 3/1979 | Wallshein | |
| 4,248,588 A | 2/1981 | Hanson | |
| 4,392,494 A | 7/1983 | Ashby | |
| 4,492,573 A | 1/1985 | Hanson | |
| 4,712,999 A | 12/1987 | Rosenberg | |
| 5,160,261 A | 11/1992 | Peterson | |
| 5,461,133 A | 10/1995 | Hammar et al. | |
| 5,470,228 A | 11/1995 | Franseen et al. | |
| 5,586,882 A | 12/1996 | Hanson | |
| 5,906,486 A | 5/1999 | Hanson | |
| 6,071,118 A | 6/2000 | Damon | |
| 6,071,119 A | 6/2000 | Christoff et al. | |
| 6,257,883 B1 | 7/2001 | Voudouris | |
| 6,368,105 B1 | 4/2002 | Voudouris et al. | |
| 6,485,299 B1 | 11/2002 | Wildman | |
| 6,632,088 B2 * | 10/2003 | Voudouris | 433/18 |
| 6,733,286 B2 | 5/2004 | Abels et al. | |
| 6,776,613 B2 | 8/2004 | Orikasa | |
| 6,932,597 B2 | 8/2005 | Abels et al. | |
| 6,935,858 B2 | 8/2005 | Cleary | |
| 6,960,080 B2 | 11/2005 | Abels et al. | |
| 6,984,127 B2 | 1/2006 | Lai | |
| 7,104,791 B2 | 9/2006 | Hanson | |
| 7,186,114 B2 | 3/2007 | Navarro et al. | |
| 7,214,057 B2 | 5/2007 | Voudouris | |
| 7,255,557 B2 | 8/2007 | Forster | |
| 7,335,020 B2 | 2/2008 | Castner et al. | |
| 2004/0072119 A1 | 4/2004 | Voudouris | |
| 2004/0166458 A1 | 8/2004 | Opin et al. | |
| 2005/0221248 A1 | 10/2005 | Navarro et al. | |
| 2006/0228662 A1 | 10/2006 | Lokar et al. | |
| 2007/0275342 A1 | 11/2007 | Oda | |
| 2007/0281269 A1 * | 12/2007 | Forster | 433/11 |
| 2008/0014544 A1 | 1/2008 | Nucera | |

* cited by examiner

*Primary Examiner* — Cris L Rodriguez
*Assistant Examiner* — Mirayda Aponte
(74) *Attorney, Agent, or Firm* — Dorr, Carson & Birney, P.C.

(57) ABSTRACT

A clip for a self-ligating orthodontic bracket assembly has a lifting element between the labial surface of the bracket and the labial portion of the clip that can be rotated to provide a range of adjustability in lifting the labial portion of the clip with respect to the bracket. The lifting element thereby controls the range of motion of the tongue of the clip in its closed position. This limits the forces applied by the clip to an archwire held in the archwire slot of the bracket, and also allows an archwire to slide freely in the slot. A threaded shaft or camming mechanism can be employed as the lifting element.

14 Claims, 8 Drawing Sheets

SELF-LIGATING ORTHODONTIC BRACKET ASSEMBLY

RELATED APPLICATION

The present application is based on and claims priority to the Applicant's U.S. Provisional Patent Application 61/094,511, entitled "Self-Ligating Orthodontic Bracket Clip," filed on Sep. 5, 2008.

BACKGROUND OF THE INVENTION

1. Field of the Invention

The present invention relates generally to the field of orthodontics. More specifically, the present invention discloses a self-ligating clip for orthodontic brackets.

2. Statement of the Problem

In the standard practice of orthodontics, a wide range of armamentarium is required including wires, springs, bands, brackets and the like. Orthodontic brackets in particular serve as the central conduit for transferring corrective forces to each individual tooth. Being rigidly connected to a tooth, corrective forces are transferred through a bracket and thereby to the root of a tooth and then to the supporting bone surrounding the root. The gentle but continuous forces elicit a physiological response in the supporting bone allowing teeth to slowly reposition. Orthodontic brackets were developed in the late 1800's, and even though manufacturing methods and basic configuration have been greatly improved, the biological functioning of orthodontic brackets remains unchanged today.

Before proceeding through the history of orthodontic brackets, it is important to understand the frame of reference commonly employed in dentistry. The term "gingival" refers to a direction toward a patient's gingiva or gum. The term "occlusal" is the opposite of "gingival" and refers to a direction toward the occlusal or incisal edge of a tooth (i.e., toward the bite plane between the upper and lower teeth). The term "mesial" (or the adjective "mesio") refers to a direction toward the mid-line of a patient's dental arch. The "distal" is the opposite of "mesial" and refers to a direction away from the mid-line of a patient's dental arch. The term "lingual" refers to a direction toward the patient's tongue. The term "labial," as applied to the front teeth, refers to a direction away toward the lips. The term "buccal," as applied to the bicuspid or molar teeth, refers to a direction toward the cheek. All of these terms are commonly used relative to a specific tooth.

The central feature of an orthodontic bracket is an archwire slot, sometimes referred to as the "slot". Two parallel walls define the slot feature, and a slot floor is oriented perpendicular to the walls. The slot feature is oriented horizontally and extends centrally across the full mesial-distal width of a bracket. Orthodontists normally place brackets on all of an orthodontic patient's teeth. The slots open to the labial or buccal aspects to accept an orthodontic archwire. The archwire spans all of the brackets by engaging the slot of each bracket. For example, U.S. Pat. No. 3,504,438 to Wittman et al. discloses orthodontic brackets with arch slots and an archwire.

It should be understood that it is the relationship between the arch slot and the archwire that drives correction of tooth position. Corrective forces are generated by the capturing of an archwire in a bracket's slot. Doing so usually requires that the archwire be deflected from its passive arcuate shape, which loads the archwire as a resilient spring. Loading in this manner causes potential energy to be stored in the archwire. It is the gradual dissipation of the stored energy that causes teeth to move into their desired, finished positions and orientations.

Generally, today's orthodontic armamentarium, and in particular, orthodontic brackets benefit from a tradition of constant improvement that has spanned many decades. In order to contain costs and to make orthodontic treatment more affordable, orthodontic practices must constantly embrace hardware systems and procedures that deliver increased efficiency. Hardware systems and chairside procedures that avoid problems, save time and eliminate steps must be embraced in order to reduce the total amount of treatment time required to treat each patient. Today's business environment requires that orthodontists become successful managers of their practices as a business as well as being skillful practitioners. One area that exemplifies the tradition of constant improvement can be seen in the means with which the orthodontic archwire is retained in the slots of the brackets. An historical review of that follows.

As mentioned earlier, orthodontic brackets were developed in the late 1800's. Beginning then and continuing through to roughly the early 1980's, archwires were routinely retained in the slots by tying-in the archwire using ligature wire. During that period, ligature wire was used in diameters ranging from 0.009 to 0.012 in. Ligature wire is fully annealed, dead-soft stainless steel exhibiting an ultimate tensile strength of about 70,000 psi. In the very soft temper and in those diameters, ligature wire is extremely malleable and can be twisted into a tight helix. FIG. 7 of U.S. Pat. No. 4,392,494 to Ashby, shows a typical Siamese-type orthodontic bracket with an archwire residing in the slot. A ligature wire engages the four tie-wings and transverses the bracket, up and over the archwire to tie it in, retaining it tightly in the slot against the slot floor. After pulling and twisting the ligature wire as tightly as required, the loose ends of the wire are cut off. The short, remaining twisted portion is tucked out of the way, under the tie wings in order to avoid laceration of soft tissue by the sharp ends. In order to perform the routine step of changing an archwire, an orthodontist or staff person must carefully repeat the procedure, usually ten times per arch, for a total of twenty times.

Steel ligatures have useful qualities that served orthodontists well. For example, in the case of a highly mal-positioned tooth, a steel ligature could first be partially tightened in a manner that avoided high deflection and the tight cinching of the archwire against the slot floor. At a subsequent appointment, the practitioner had the option of then fully tightening the ligature. Such tightening of steel ligatures allowed the progressive tightening to match desirable tooth movement response achieved over several weeks, such as the interval between patient appointments. Had the practitioner fully tightened the ligature initially, the patient would likely have experienced significant discomfort, and the resulting higher than optimal forces could have actually resulted in a slower tooth movement rate. Orthodontic patients treated with steel ligatures were often scheduled for appointments where the objective was to simply tighten all of the ligatures. Such a tightening served to more aggressively transfer stored energy from the deflected archwire to the brackets and teeth.

Other common procedures took advantage of the characteristics of steel ligatures. For example, in the case of a highly-rotated tooth, the practitioner had the option of using only the distal pair or mesial pair of tie wings for ligation rather than the conventional use of all four wings. Selectively using only one pair of tie wings created an advantageous moment in rotation, which was capable of more effectively correcting a tooth in terms of rotation. Progressively tightening a ligature that was placed for rotation was an ideal method for correcting rotated teeth. Steel ligatures, not being of any set length, could take up the length of tying two wings or the longer route of four wings. Doctors and staff became very accustomed to characteristics of steel ligatures and skills associated with ligation facilitated treatment well.

In cases with teeth generally well oriented in terms of torque and rotation, but requiring translation to a new position, steel ligatures once again filled the need well. In those cases, the bracket and its corresponding tooth would be ligated closely to the archwire, but not tightly. This would permit the tooth to remain under the influence of the archwire-archslot relationship while sliding along the archwire in response to tractive forces such as an elastic or steel coil spring. During such sliding, the tight but free-sliding ligature around the archwire would keep the bracket oriented on track, but the steel ligature would be configured loosely enough so as to not create excessive binding or undue friction. Conversely, once the tooth arrived at its ideal position, the ligature could be fully tightened. Such tightening served to greatly increase the sliding friction between the archwire and the bracket. In this way, steel ligatures could be used to allow a bracket to slide freely to its desired position, then once arriving there, lock it in place. Such a methodology served well such as in closing extraction spaces.

Even though dead-soft stainless steel ligatures served quite well for many years, the shortcomings became more problematic as other areas of the orthodontic operatory became modernized. Orthodontists began treating much larger numbers of patients and steel ligatures did not fit well into the streamlined needs of a fast-paced orthodontic practice. The amount of time required to change an archwire became excessive compared to other advancements. After all, steel ligatures require special instruments, and tying an archwire to each tooth is time consuming. Further, if each ligature is not placed with care and not cut and tucked properly, the patient's tongue, lips or cheeks can be painfully pierced. Even though steel ligatures are still used today for certain treatment situations, they have by and large been supplanted by elastomeric ligatures.

For example, U.S. Pat. No. 6,935,858 (Cleary) shows a typical orthodontic case with the archwire retained with elastomeric ligatures. Like steel ligatures, elastomeric O-rings are placed to hold the archwire fully seated in the bracket slots. Elastomeric ligatures are non-metallic and are injection molded from biocompatible, low-durometer urethane resins. Orthodontic manufacturers typically offer a family of elastomeric products. Central to such product lines are the ligatures, which can take on any combination of cross-sectional diameter and toroidal diameter required to fit a range of narrow-to-wide brackets. The man-made elastomeric resins used are generally slightly stiffer/harder than the familiar natural latex "rubber bands" used in orthodontics.

Elastomeric ligatures are typically molded integrally with a carrier and each ligature is connected to the carrier by a thin runner or sprue. Once the ligature is hooked over one wing of a bracket, the practitioner can fail the sprue by pulling the carrier away. Elastomeric ligatures are also commercially available individually, along with special placing instruments. As described, commercial sources of ligatures typically offer a family of elastomeric products molded from the same elastomer. U.S. Pat. No. 5,461,133 (Hammar et al.) discloses some of the other types of orthodontic products typically offered along with elastomeric ligatures, including chains and rotation wedges. Elastomeric urethane materials are commercially available in many configurations and sizes as well as a wide array of colors, including metal flake and glow-in-the-dark versions. Such offerings allow orthodontic patients the option of self-expression, which is thought to increase the patient's cooperation with treatment objectives.

The use of small elastomeric ligatures bypasses the steps of twisting, cutting and tucking as is required when using steel ligatures. Each elastomeric ligature is initially caught by one of the bracket's tie wings and then stretched over the other tie wings. No additional steps are required to ligate-in the archwire.

Compared to steel ligatures, elastomeric ligatures do not have quite as much adjustability and versatility. For example, steel ligatures were described earlier as allowing a close, but still sliding relationship between a bracket and an archwire for cases where teeth must be bodily translated along an archwire. Being stretched in place between the tie wings and over the archwire, elastomeric ligatures are always in tension and therefore continuously urging the archwire against the slot floor. Such constant working of an elastomeric ligature serves well for rotating and torqueing teeth, but such forces are not as desirable when low friction and sliding translation is needed. In most treatment situations elastomeric ligatures cannot be held off, and do not allow the option of progressive tightening, and cannot be adjusted in any way.

In spite of the merits of steel versus elastomeric ligatures, it is the elastomeric version that has been adopted as today's default standard by the orthodontic profession due to efficiency and speed. Orthodontic staff can change-out an archwire much more quickly compared to the time required using steel ligatures.

Further advancements in the orthodontic armamentarium have resulted in the self-ligating bracket. Such brackets are designed with newer features that eliminate the need for any sort of ligature all-together. The first successfully functioning self-ligating bracket was developed by Ford, and was disclosed in 1935 through U.S. Pat. No. 2,011,575. Ford's invention disclosed a bobbin, that when rotated clockwise aligned with other structures allowing an archwire to drop into the slot, but after rotating the bobbin counter-clockwise, the wire is retained. Even though Ford's self-ligating bracket (known as the "Ford lock") was commercialized, it did not see widespread popularity. This was likely because today's impetus for speed and efficiency was not as critical in Ford's day.

The first self-ligating bracket to achieve widespread commercial success was developed by a Canadian orthodontist, G. H. Hanson. Hanson's development was disclosed in U.S. Pat. No. 4,492,573 issued in 1985. Improvements thereto have been disclosed by other patents to Hanson, such as U.S. Pat. No. 5,586,882. Appropriately, Hanson's bracket design is marketed as the "Speed Bracket" as it is known today. The Speed Bracket is very popular with orthodontists world-wide because it further reduces the time required to accomplish the task of changing-out an archwire. The Speed Bracket has an occlusal-gingivally sliding clip. With the clip positioned occlusally, the bracket is considered to be in the open configuration to accept an archwire. With the clip positioned gingivally, the bracket is in its closed configuration to retain an archwire. Certain features serve to bias the clip in the open or closed positions.

As a category, self-ligating brackets have become an important adjunct to today's armamentarium. The designs offered by orthodontic manufacturers have advanced, overcoming the early problems such as tartar build-up blocking the smooth sliding of clips, clips that would not stay open or stay closed, clips that could become loose in the mouth, and the increased bulk and height of self-ligating brackets compared to conventional brackets.

When considering the entire category of self-ligating brackets, they can be further classified into groups based on the mechanical means for achieving ligation. For example, U.S. Pat. No. 4,712,999 to Rosenberg describes a self-ligating bracket with a cover plate that resiliently engages a corresponding cylindrical section of the bracket. Rosenberg's clip is a separate part, and hinges open and closed once in position. An improvement over Rosenberg is exemplified by a living hinge. For example, U.S. Pat. Nos. 6,733,286, 6,932,597, 6,960,080 and many subsequent patents to Abels et al. disclose a ligation cover integrally attached to the base of the bracket as one piece that moves between an open and closed position. Yet other innovative means for self-ligation utilize a true fixed hinge for the clip. Even though depicted as an adjunct to lingual brackets, U.S. Pat. No. 6,485,299 (Wildman) discloses such a hinging clip. U.S. Pat. No. 6,984,127 to Ming discloses a self-ligating bracket based on a resilient latch that can retain an archwire once an archwire is forced into the latch.

As can be appreciated, many inventors have contributed improvements to the field of self-ligating brackets and today there are multiple categories of such brackets, each delineated by the specific means used for securing the archwire in the slot. The present invention is directed to one of these categories of self-ligating brackets. First, to describe the category:

One example of the relevant category of self-ligating brackets is taught by U.S. Pat. No. 6,071,119 (Christoff et al.). This bracket 20 consists of a rigid bracket body through which passes a mesial-distal extending arch slot 30 shown with an archwire 40a residing in the slot. A one-piece movable latch 32 has a labial portion 34a and a sliding portion 36a. The bracket body 24 includes a retentive lip 44a and a stop 46a. The movable latch typical of this category of self-ligating brackets is usually formed from spring-temper metal and as such it is biased inwardly, toward the arch slot, serving to actively restrain the archwire from escaping from the slot. Such clips may be formed from AISI type 410 stainless steel or 17-7 ph, a stainless alloy. Once formed, sliding clips can be heat treated to a near spring temper and as such, the force level required to deflect the labial portion outward can be significant. As such, the labial portion of the latch can be considered as "active" in that with sufficient labially or buccally-directed force, it can flex outward away from the archwire slot floor to the extent that it is restricted from further outward flexing by a retentive lip feature 44a of the bracket body according to Christoff et al.

FIG. 9 of U.S. Pat. No. 7,104,791 to Hanson similarly shows a movable latch moved to its closed position. The movable latch is configured similarly to the invention of Christoff et al., having features that limit the range of lingual-labial or lingual-buccal flexing of the labial portion, and an inward or lingual spring bias of the labial portion of the latch.

U.S. Pat. No. 7,186,114 to Navarro et al. shows yet another movable latch in a closed position (FIG. 4a) and in an open position (FIG. 4c). FIG. 4a depicts the archwire-retaining portion of the movable latch 38 positioned in its lingual-most position, limited from further lingual movement by the edge of the recess 48. As can be appreciated, should treatment forces act on the archwire to lift the archwire out of its slot 28, the archwire will be urged back into a seated position in the slot due to the lingual bias and resilience typically observed in such sliding latches used with self-ligating brackets of this category. However, if the forces acting to lift the archwire exceed the resilience of the labial portion of the latch, the latch can open only to the other end of its range as defined by the lip of the recess 48. The latch flexure-limiting function of the recess 48 is substantially identical to the retentive lip 44a of Christoff et al.

U.S. Pat. No. 7,214,057 to Voudouris shows yet another self-ligating bracket with a sliding latch. Of importance when considering the present invention, the reader should note the wide tongue portion of the clip located generally above numeral 94 in FIG. 11 of the Voudouris patent. It is important to visualize the tongue portion as engaging the same sort of retentive lip functioning as feature 44a and 46a shown by Christoff et al.

The present invention can be viewed as an improved movable latch of the same general type as those disclosed by these prior art patents. To best describe and illustrate the benefits and advantages of the present invention, FIGS. 1-7 show a consolidation of the sliding latch-type features from these prior art patents into a hypothetical composite configuration. In particular, FIG. 1. shows a moving latch 10 that is a composite of the features of the clips of the prior art patents discussed above. For the purposes of this disclosure, the terms "clip" and "latch" are used interchangeably.

FIG. 2 shows the composite sliding latch 10 in place in its closed position within the body of the composite bracket 20. The tail 16 of the latch 10 is a disrupted feature, usually formed as a press operation that serves as a stop for the latch 10. The stop limits sliding of the clip 10 as it reaches its fully open position and prevents the clip 10 from becoming dislodged from the bracket 20.

As pointed out earlier, during the manufacture of such brackets 20, the sliding latch 10 is hardened to a near-spring temper and as such, it maintains a shape that when in position biases the tongue 18 of the clip 10, inward or lingually, as shown in FIGS. 2 and 3.

In FIG. 4, the tongue 18 of the clip 10 is acting on a light, round archwire 30, urging it lingually, and cinching it against the slot floor formed in the rigid bracket body 20. Such a configuration is useful for controlling a pliable, smaller-diameter round wire 30 such as is typically placed by orthodontists early in treatment. The configuration of the tongue 18 in FIG. 4 enables it to push lingually against the round archwire 30. Thus, the tongue 18 of the clip 10 is well positioned to actively capture the archwire 30, and thereby transfer forces from the archwire 30 to the root of the tooth.

The meaning of the term "active", as it applies to movable latches, can be explained as follows. Earlier, steel ligatures were described and in particular the practice of progressively tightening steel ligatures with the steel ligature engaging only one of the two pairs of ligation wings of a standard orthodontic bracket was described. That practice served as a means for correcting tooth position in terms of rotation. Later, the elastomeric ligatures were described as also being capable of engaging only one pair of the two pairs of tie wings of a conventional bracket. For self-ligating brackets, rotation correction is instead pursued using the "active" qualities of the sliding latch. As can be appreciated, the lingual or inward biasing of the latch's tongue 18 against a smaller round archwire 30 tends to trap such an archwire against the slot 21 floor. In cases where the tooth is undesirably rotated, the spring resilience of the sliding latch 10 attempts to deflect the archwire 30 into an "S" shape as it spans the brackets on adjacent teeth, as illustrated in FIG. 5. By deflecting the archwire 30 in that manner, it loads the archwire 30 to de-rotate the tooth.

During actual treatment situations, the latch's tongue 18 may become angled so as to be in a non-parallel relationship to the slot floor. Such a deflection may last for several weeks, but as the tooth slowly responds to these forces and de-rotates toward its desired orientation, the tongue slowly returns to its parallel relationship to the slot floor. It is the constant spring-biasing by the movable latch 10 and its tongue 18 against an archwire 30 that is considered to be the "active" quality. In summary, it is the labial-lingual flexing, along with twisting as depicted in FIGS. 5 and 6 resulting from constant dynamic interplay with the archwire 30 that defines an active sliding latch 10. The commercial success of such self-ligating brackets of the type taught by the prior art is due largely to the effectiveness of the active-biased sliding latches.

Later in treatment, for final aesthetic positioning of the teeth, orthodontists typically use larger wires exhibiting a stiffer temper. Such wires are sometimes called "finishing wires". Finishing wires exhibit a rectangular cross-section profile. One popular example of the dimensions of such wires is 0.021×0.025 in. An example is depicted in FIG. 7. When such wires are seated in the arch slot of a conventional self-ligating bracket, the tongue of the sliding latch is held up, further away from the slot floor. As such, the lingual or inward biasing of the sliding latch tongue becomes even more aggressive, acting to force the finishing wire even more forcefully against the slot floor.

Earlier, recess 48 of FIG. 4a of U.S. Pat. No. 7,186,114 (Navarro et al.) was discussed. The recess 48 in Navarro et al. limits the range of flexure of the tongue of the sliding latch. As can be appreciated from Navarro et al., the tongue portion of the latch may rest on the lingual-most edge of the recess 48 during early treatment when a small round archwire resides in the arch slot, but the tongue may rest near the labial-most edge of the recess 48 near the end of treatment.

The acceptance and wide use of self-ligating brackets represents an important advancement in orthodontics. There is however one notable shortcoming in spite of the popularity of conventional self-ligating brackets. The problem is similar to the lack of adjustability and versatility associated with the elastomeric ligatures described earlier. Both elastomeric ligatures and active sliding latches cannot be regulated or moderated in any way, and as such they are constantly applying cinching forces to the archwire. An unavoidable result of such constant working is sliding friction between the archwire and a tooth/bracket in translation. Excessive friction between a bracket and an archwire is undesirable in orthodontics and some researches believe that even slight friction and hysteresis in the relative movement of the archwire in the slot can dramatically slow bodily tooth movement. In response to the friction problem, considerable innovation has occurred as low-friction and zero-friction bracket designs have been promulgated. U.S. Pat. No. 5,470,228 to Franseen et al. and U.S. Pat. No. 5,160,261 to Peterson disclose various innovative features directed toward reducing such friction. In the orthodontic lexicon, the term "sliding mechanics" applies to the issues associated with friction between brackets and archwires and other areas of orthodontic hardware. It is common for orthodontic treatment plans to accommodate the extraction of teeth for arch development, and subsequently, the serial distalization of the upper arch. These are examples of treatment phases where teeth must be translated bodily along an archwire and the considerations of sliding mechanics apply.

In addition to greatly inhibiting tooth translation rate, tight binding of the bracket to the archwire can also restrict the mobility of a tooth, causing it to be positioned in an unnaturally rigid way in its supporting bone. Such rigidity of course prevents the normal mobility of the root of a tooth within the elastic periodontal ligament. Such rigidity can undesirably impact blood circulation and the general vitality of the region of bone supporting the tooth. The amount of movement of teeth during eating, speaking and so on would surprise most people, who may have the impression that teeth are rigid. Quite to the contrary, teeth naturally wiggle in position in response to forces. The sliding friction resulting from the stiff resilience of the latch's tongue acting against the archwire and the additional friction of the archwire against the arch slot floor can be a significant impediment to a treatment plan and treatment schedule.

Solution to the Problem. These concerns involving sliding mechanics are addressed by the present invention. The present invention introduces a means for regulating the aggressiveness of rotational forces not unlike the adjustment latitude afforded by steel ligatures described earlier. The present invention also allows a free-sliding relationship between the archwire and the bracket. In addition, with the present invention, the active (and friction-inducing) qualities of the labial portion of the sliding clip can be selectively restored as required over the course of treatment by adjusting a rotating lifting mechanism.

SUMMARY OF THE INVENTION

This invention provides a clip for a self-ligating orthodontic bracket assembly having a lifting element between the labial surface of the bracket and the labial portion of the clip that can be rotated to provide a range of adjustability in lifting the labial portion of the clip with respect to the bracket. The lifting element thereby controls the range of motion of the tongue of the clip in its closed position. This limits the rotational forces applied by the clip to an archwire held in the archwire slot of the bracket, and also allows an archwire to slide freely in the slot. A threaded shaft or camming mechanism can be employed as the rotating lifting element.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

Figure 1:
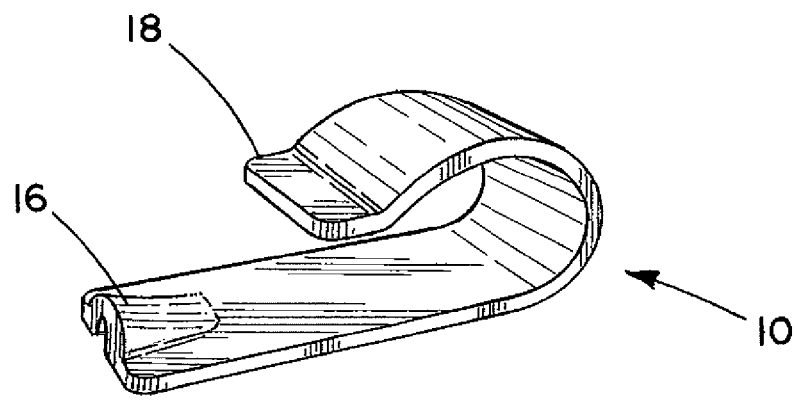
FIG. 1 is a perspective view of a conventional clip 10 for a self-ligating orthodontic bracket.
Figure 2:
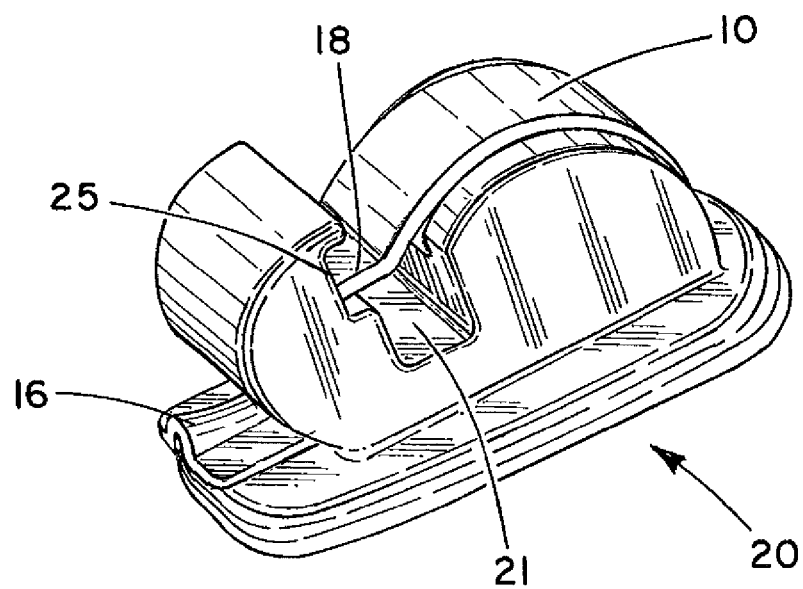
FIG. 2 is a perspective view of a conventional self-ligating bracket 20 and clip 10 in the closed position.
Figure 3:
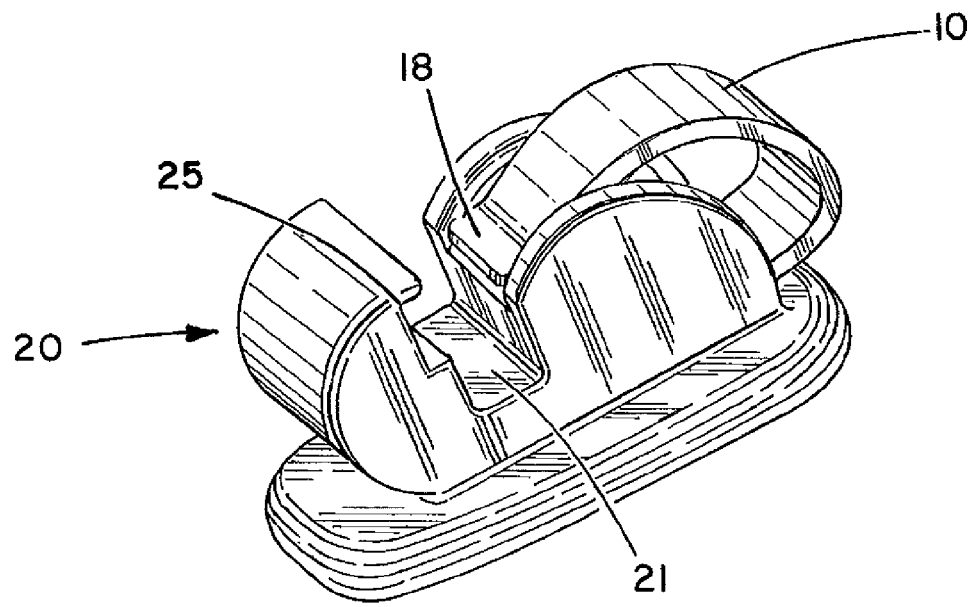
FIG. 3 is a perspective view of a conventional self-ligating bracket 20 and clip 10 in the open position.
Figure 4:
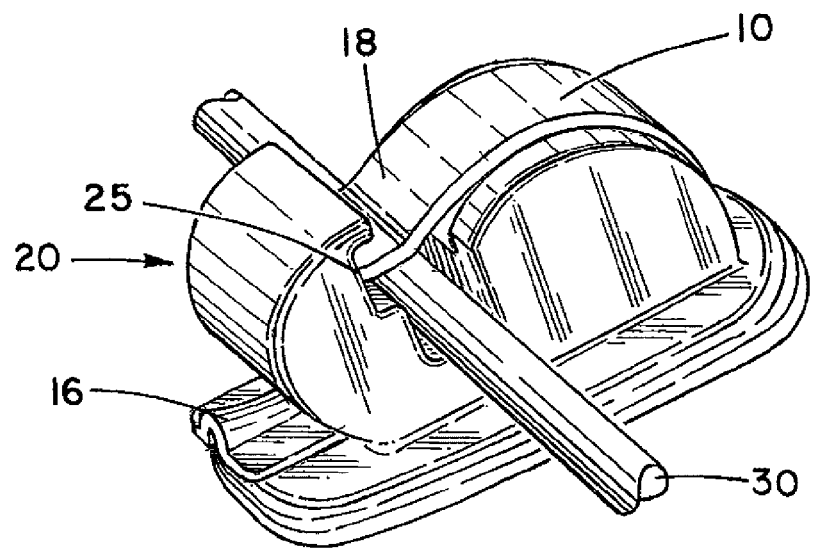
FIG. 4 is a perspective view of a conventional self-ligating bracket 20 and clip 10 in the closed position holding a round archwire 30.
Figure 5:
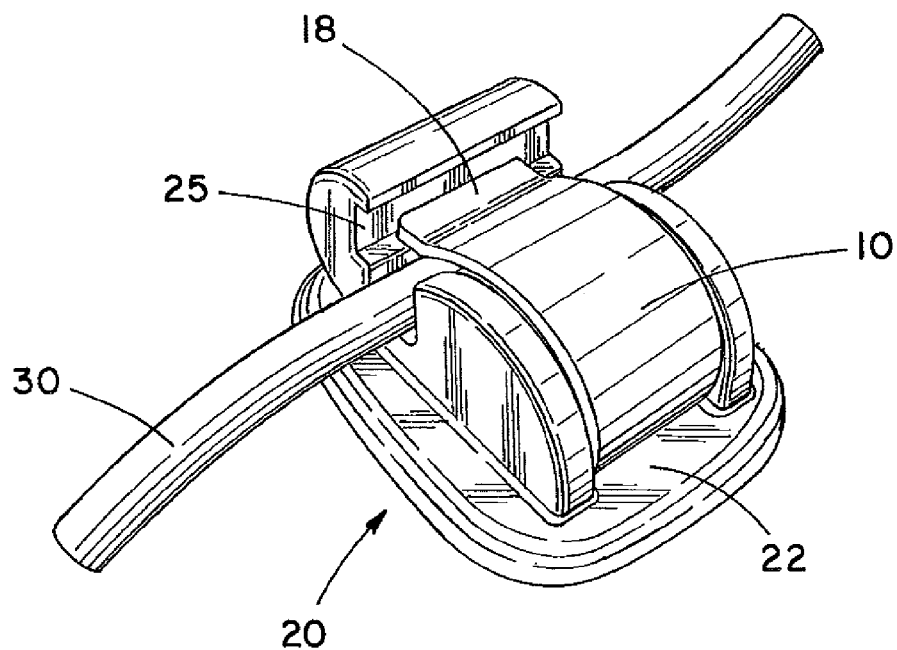
FIG. 5 is a perspective view of a conventional self-ligating bracket 20 and clip 10 in the closed position holding an archwire 30 that has been deflected into an "S" shape by a rotated tooth.
Figure 6:
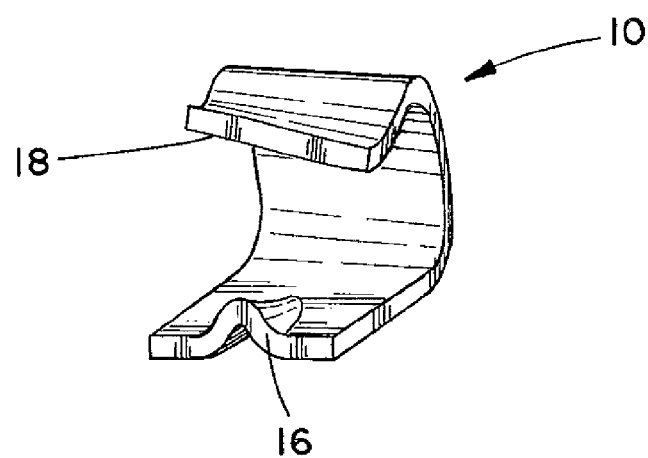
FIG. 6 is a perspective view of the clip 10 corresponding to FIG. 5.
Figure 7:
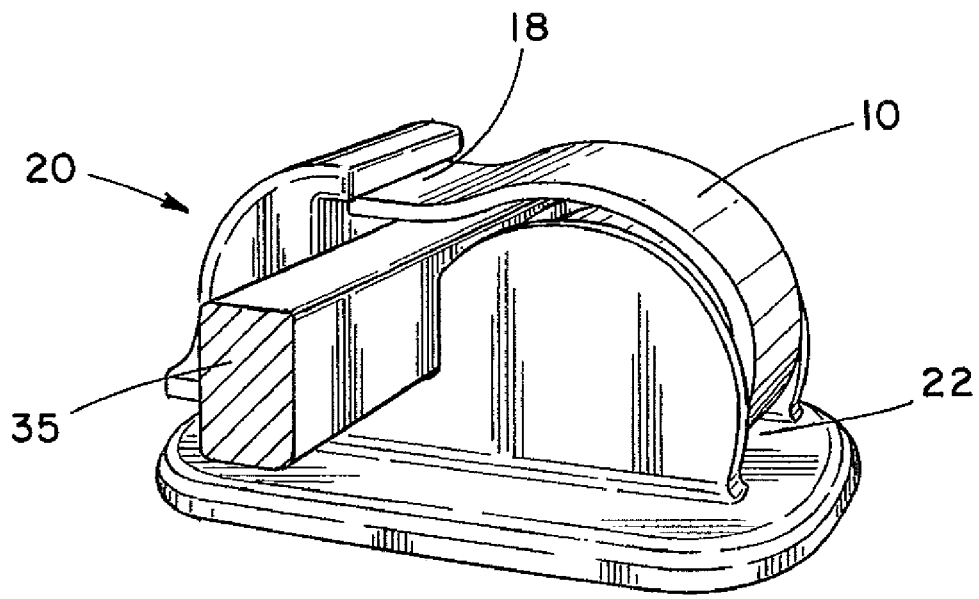
FIG. 7 is a perspective view of a conventional self-ligating bracket 20 and clip 10 holding a finishing archwire 35.

FIGS. 8-12 show an embodiment of the present invention that employs a threaded lifting element 14 to adjustably lift the labial portion of the clip 10 from the labial surface of the bracket 20. This, in turn, adjusts the force exerted by the tongue 18 of the clip 10 on an archwire 30 in the archwire slot 21. The major components of this embodiment are the bracket 20, sliding clip 10, and a rotatable lifting element 14.

Figure 8:
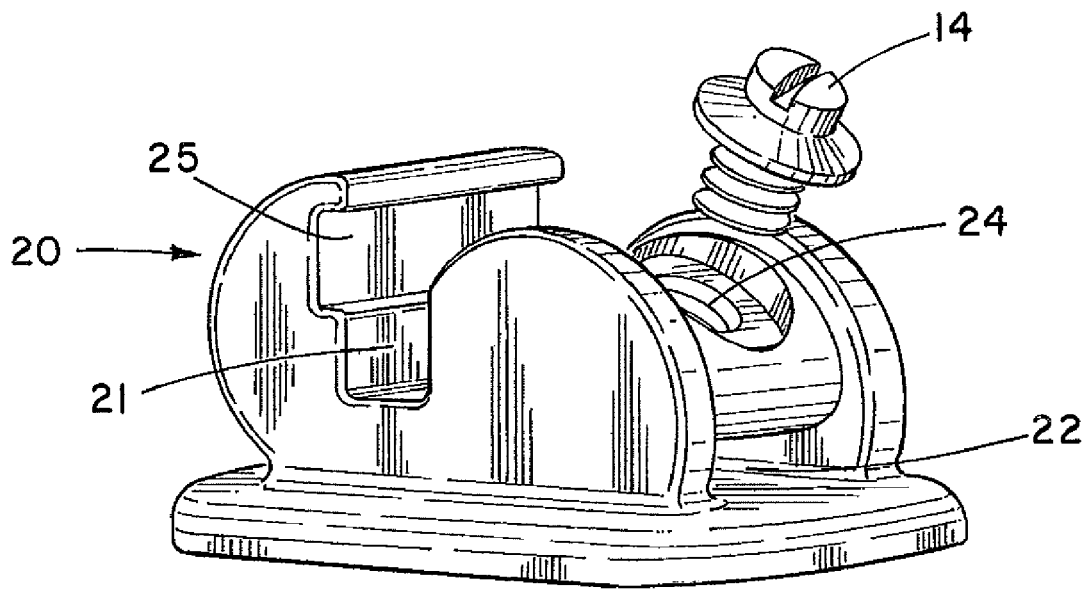
FIG. 8 is an exploded perspective view of an embodiment of the present invention showing a bracket 20 having a threaded hole 24 to receive a threaded lifting element 14.
Figure 11:
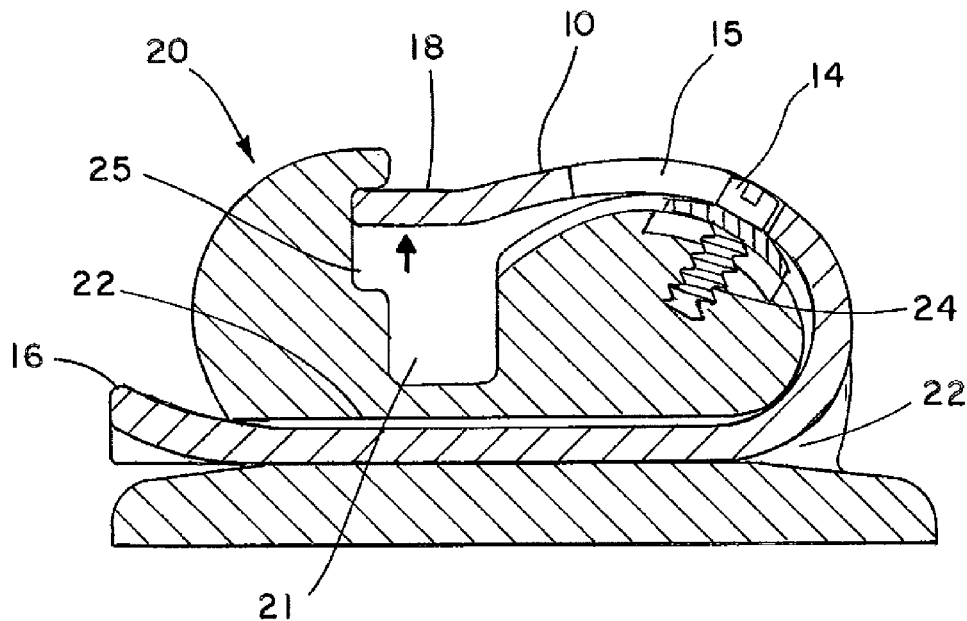
FIG. 11 is a side cross-sectional view corresponding to FIG. 9 with the lifting element 14 adjusted to raise the tongue 18 of the clip 10 to a passive position.
Figure 12:
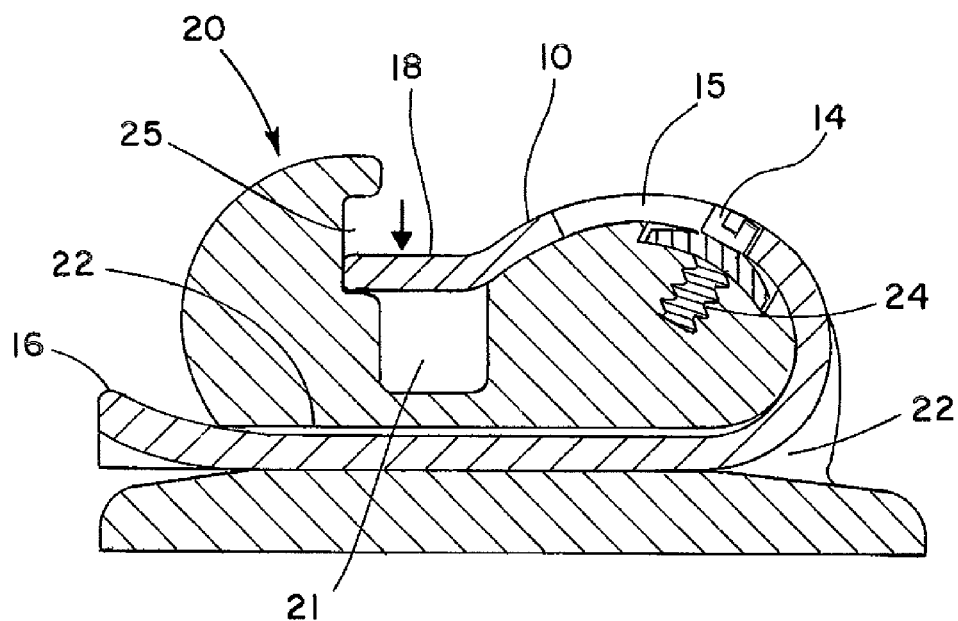
FIG. 12 is a side cross-sectional view corresponding to FIGS. 9 and 11 showing the lifting element 14 fully threaded into the bracket 20, thereby allowing the tongue 18 of the clip 10 to move to an active position.

The bracket 20 is shown in FIG. 8. The base has a conventional base for attachment to a tooth (e.g., by adhesive). An archwire slot 21 extends in a substantially horizontal, or mesio-distal direction across body of the bracket 20 with an open labial aspect to receive an archwire. The archwire slot 21 can have a cross-section forming three sides of a rectangle, as shown in FIGS. 8, 11 and 12, to better engage an archwire with a rectangular cross-section. A channel 22 extends through the bracket 20 in an occlusal-gingival direction behind the archwire slot 21. The labial surface of the occlusal portion of the bracket 20 has a curved contour to follow the contour of the labial portion of the clip 10, as will be discussed below. The bracket 20 also includes a recess 25 adjacent to the archwire slot 21 for receiving the tongue 18 of the clip 10 in its closed position. The labial surface of the bracket 20 features a threaded hole 24 to engage the lifting element 14.

Figure 9:
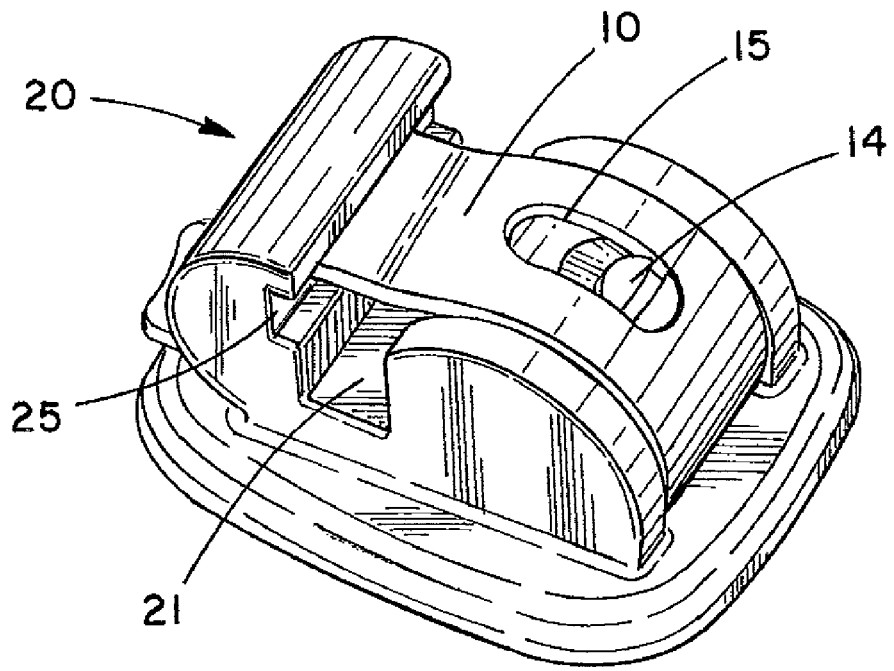
FIG. 9 is a perspective view showing the embodiment in FIG. 8 after it has been assembled.
Figure 10:
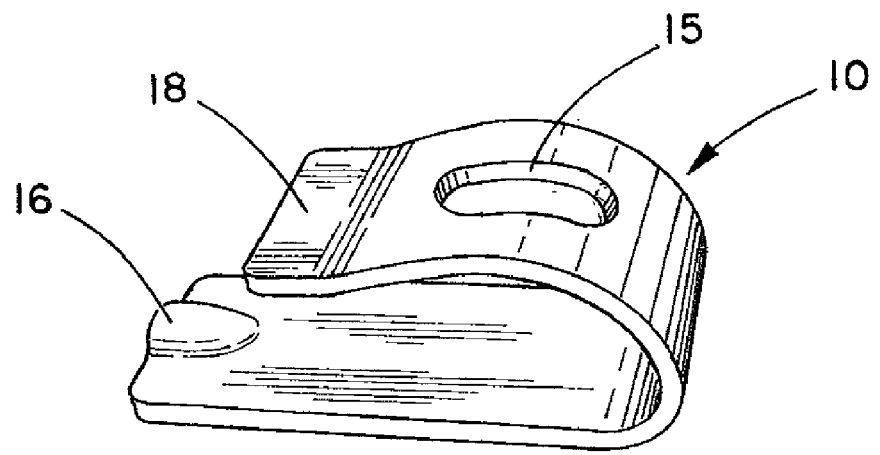
FIG. 10 is a perspective view of the clip 10.

Preferably, the clip 10 is generally J-shaped as shown in the perspective view in FIG. 10. The back of the J forms the lingual aspect of the clip 10 and has dimensions selected to allow the lingual portion of the clip 10 to slide within the channel 22 of the bracket 20 between the clip's open and closed positions. A stop 16 is located at the stem of the J to prevent the clip 10 from becoming dislodged from the bracket 20. The labial aspect of the clip 10 can be curved to generally match the labial contour of the curved occlusal portion of the bracket 20. The tongue 18 of the clip 10 is designed to seat in the recess 25 of the bracket 20 when the clip 10 is in the closed position, as shown in FIGS. 9, 11 and 12.

The rotatable lifting element 14 has a threaded shaft with an enlarged head (e.g., a screw or bolt), as shown in FIG. 8. The threads of the lifting element 14 engage the threaded hole 24 in the labial surface of the bracket 20. FIG. 9 is a perspective view showing the embodiment in FIG. 8 after it has been assembled. The head of the lifting element 14 rests under the lingual surface of the labial portion of a clip 10, and serves to lift the lingual surface of the labial portion of the clip 10 away from the labial surface of the bracket 20. The degree of lift is controlled by rotating the lifting element 14 clockwise to lower the clip 10 or counter-clockwise to raise the clip 10.

As can be seen in FIG. 9, the head of the lifting element 14 rests under the curved lingual surface of the labial portion of the clip 10 when the clip 10 is in its closed position. As the lifting element 14 is loosened, the head of the lifting element 14 serves to lift the tongue 18 of the clip 10 to an intermediate or passive position in the recess 25 in the bracket 20. FIG. 11 is a side cross-sectional view corresponding to FIG. 9 with the lifting element 14 adjusted to raise the tongue 18 of the clip 10 to a passive position. In this passive state, the tongue 18 is incapable of exerting cinching forces on the archwire 30. Even though the tongue 18 is poised near the archwire 30 in the slot 21, no forceful contact occurs except in situations where the tooth is undesirably rotated. Lacking contact due to rotation, the archwire 30 is allowed to slide freely in the archwire slot 21 of the bracket 20. The deleterious effects described earlier resulting from holding the tooth rigidly and lack of mobility are thereby avoided. Treatment phases requiring translation of the teeth may be accomplished while still controlling the tooth's orientation and inclination.

Later in treatment as the aesthetic finishing phase approaches, an orthodontist may wish to return the bracket 20 to active functioning. To do so, the lifting element can be threaded further into the bracket, thereby lowering the tongue 18 of the clip to the active position shown in FIG. 12, so that the tongue 18 exerts resilient force on the archwire 30. In this state, the clip 10 functions like any sliding latch of conventional self-ligating brackets. The tongue 18 of the clip 10 delivers exacting forces to the archwire 30, serving to position the tooth in its final ideal position.

Thus, the threaded lifting element 14 can be readily adjusted inward or outward to achieve any needed balance between passive or active functioning of the clip's tongue 18 against an archwire 30. The lifting element 14 shown in FIGS. 8 and 9, can be adjusted as desired over the course of treatment using a jeweler's screwdriver. Alternatively, the means for adjusting the threaded lifting element 14 can be a hex-socket Allen-type engagement, torqs, hexagonal bolt head, Phillips head, or other standard means.

As can be seen in FIGS. 9 and 10, an elongated slot 15 can be formed in the clip 10 to allow the adjustment features of the threaded lifting element 14 to be accessible, and to allow the sliding clip 10 to move between its open and closed positions. This slot 15 is envisioned as serving dual functions. For example, the portion of the threaded lifting element 14 protruding into and above the slot 15 in the clip 10 may also serve as a stop, establishing the range of the open and closed positions of the clip 10. This auxiliary function may eliminate the need for traditional means for limiting travel of the clip. Further, the threaded lifting element 14 may serve to bias the clip 10 in an open or closed position.

It should be understood that other mechanisms could be substituted in place of the threaded lifting element 14 in the embodiment depicted in FIGS. 7-12. In particular, any of a variety of screw mechanisms could be employed to lift the lingual surface of the labial portion of the clip 10 from the labial surface of the bracket 20.

Figure 13:
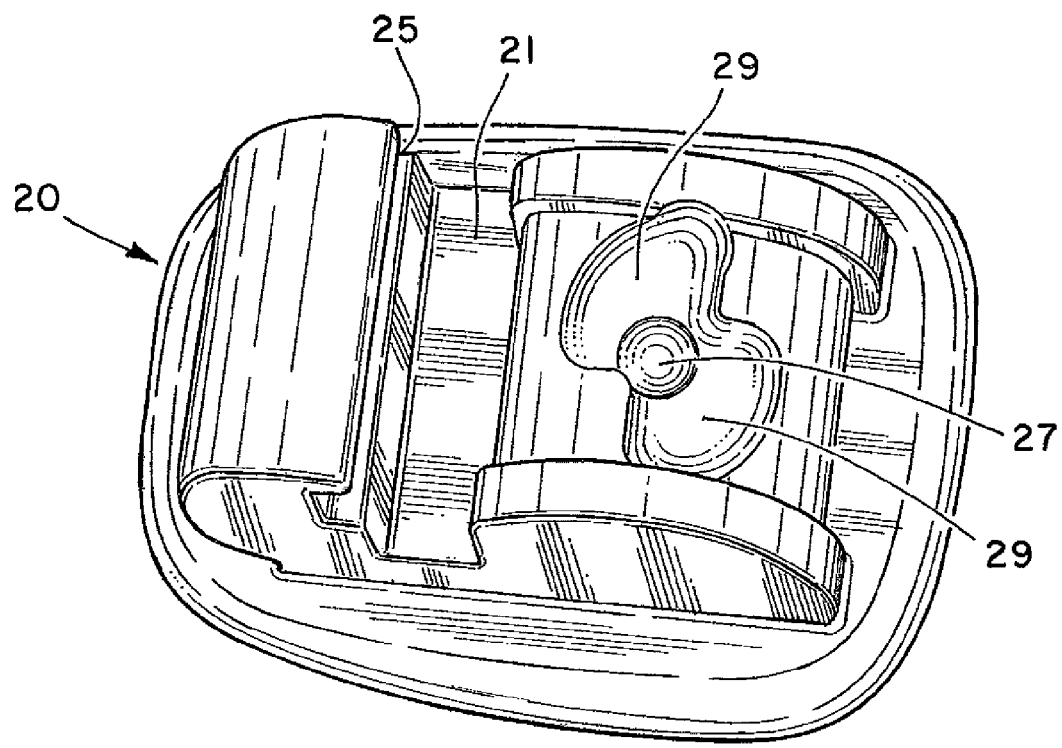
FIG. 13 is a perspective view of another embodiment of a bracket 20 having a hole 27 with camming surfaces 29 to actuate a lifting element.
Figure 14:
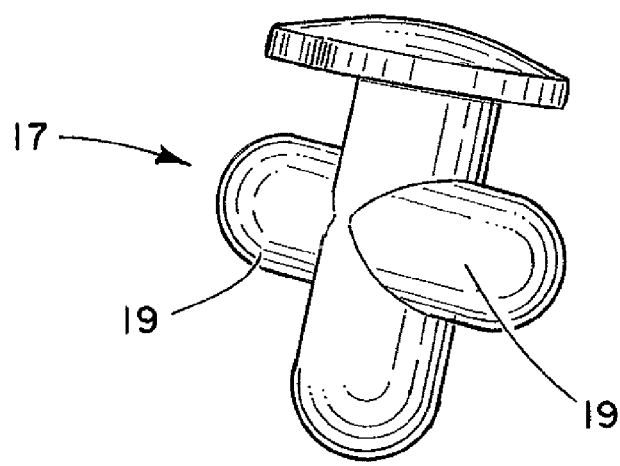
FIG. 14 is a perspective view of a lifting element 17 for use with the camming surfaces 29 of the bracket 20 in FIG. 13.

For example, one alternative shown in FIGS. 13-16 employs a set of rotational camming surfaces 29 in a radial pattern formed in the labial surface of the bracket 20 to engage and actuate a lifting element 17 that is held between the bracket 20 and the lingual surface of the labial portion of the clip 10. As shown in FIG. 14, the lifting element 17 in this embodiment has a central shaft that seats in a hole 27 in the labial surface of the bracket 20, and two arms 19 extending outward from the shaft. The arms 19 ride on the camming surfaces 29 arranged in a radial pattern about the central hole 27. The camming surfaces 29 cause the lifting element 17 to raise or lower the tongue 18 of the clip 10 as the lifting element 17 is rotated. FIG. 13 is a perspective view of the bracket 20 showing the hole 27 and camming surfaces 29. The lifting element 17 can be progressively adjusted over the course of treatment, if desired, by rotating the head of the lifting element 17 with pliers or forceps. The camming surfaces 29 could also be designed so that the lifting element can be rotated between its active and passive positions, but will tend not to remain in an intermediate position.

Figure 15:
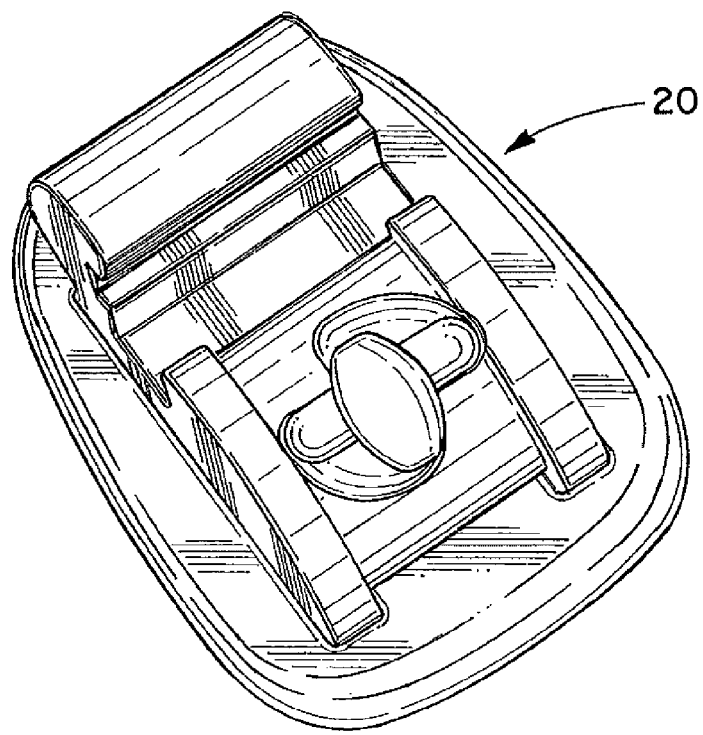
FIG. 15 is a perspective view of the lifting element 17 assembled with the bracket 20.
Figure 16:
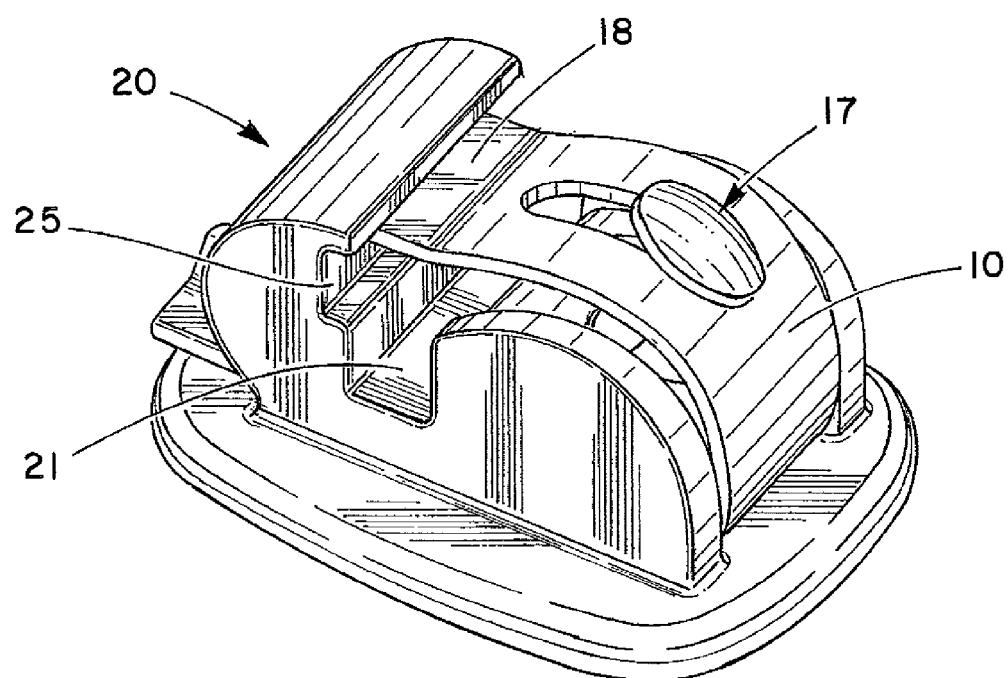
FIG. 16 is a perspective view of the completed assembly of the clip 10, bracket 20 and lifting element 17.

With either embodiment, the head of the lifting element can have an oblong or elongated shape as shown in FIGS. 15 and 16 to serve as a visual indicator. At a glance, the orthodontist or staff can easily ascertain the bracket's active or passive status from the rotational position of the head of the lifting element. The head of the lifting element 17 can also include a hex-socket Allen-type engagement, torqs, hexagonal bolt head, Phillips head, or other standard means for rotating the lifting element 17.

These lifting mechanisms can be generalized to include virtually any type of screw or rotating camming mechanism that can formed or placed between the labial surface of the bracket 20 and lingual surface of the labial portion of the clip 10. For the purposes of this disclosure, the term "lifting element" is intended to encompass all such mechanisms.

The above disclosure sets forth a number of embodiments of the present invention described in detail with respect to the accompanying drawings. Those skilled in this art will appreciate that various changes, modifications, other structural arrangements, and other embodiments could be practiced under the teachings of the present invention without departing from the scope of this invention as set forth in the following claims.

I claim:

1. A self-ligating orthodontic bracket assembly comprising:
    a bracket having:
    (a) an archwire slot extending mesio-distally across the bracket for receiving an archwire;
    (b) a channel extending through the bracket in an occlusal-gingival direction; and
    (c) a labial surface;
    a clip having:
    (a) a back forming the lingual aspect of the clip, sliding within the channel of the bracket between an open position and a closed position for the clip;
    (b) a labial portion; and
    (c) a tongue extending from the labial portion of the clip across the archwire slot when the clip is in the closed position, and being retracted from the archwire slot when the clip is in the open position; and
    a rotatable lifting element having a threaded shaft threaded into the labial surface of the bracket adjustably lifting the labial portion of the clip from the labial surface of the bracket, thereby adjusting the force exerted by the tongue of the clip on an archwire in the archwire slot.

2. The self-ligating orthodontic bracket assembly of claim 1 wherein the clip is substantially J-shaped.

3. The self-ligating orthodontic bracket assembly of claim 1 wherein the labial portion of the clip is contoured to follow the contour of the labial surface of the bracket.

4. The self-ligating orthodontic bracket assembly of claim 1 wherein the lifting element further comprises a head lifting the labial portion of the clip.

5. The self-ligating orthodontic bracket assembly of claim 4 wherein the clip further comprises a slot through the labial portion of the clip providing access to the head of the lifting element.

6. The self-ligating orthodontic bracket assembly of claim 5 wherein the slot through the labial portion of the clip has a length selected to limit the range of travel of the clip between the open and closed positions.

7. A self-ligating orthodontic bracket assembly comprising:
    a bracket having:
    (a) an archwire slot extending mesio-distally across the bracket for receiving an archwire;
    (b) a channel extending through the bracket in an occlusal-gingival direction;
    (c) a labial surface; and
    (d) camming surfaces in a radial pattern on the labial surface of the bracket;
    a clip having:
    (a) a back forming the lingual aspect of the clip, sliding within the channel of the bracket between an open position and a closed position for the clip;
    (b) a labial portion; and
    (c) a tongue extending from the labial portion of the clip across the archwire slot when the clip is in the closed position, and being retracted from the archwire slot when the clip is in the open position; and
    a lifting element rotating on the camming surfaces between the clip and the bracket to adjustably lift the labial portion of the clip from the labial surface of the bracket and thereby adjust the force exerted by the tongue of the clip on an archwire in the archwire slot.

8. The self-ligating orthodontic bracket assembly of claim 7 wherein the lifting element comprises a central shaft and at least one arm extending outward from the central shaft to slide on a camming surface.

9. The self-ligating orthodontic bracket assembly of claim 7 wherein the clip is substantially J-shaped.

10. The self-ligating orthodontic bracket assembly of claim 7 wherein the clip further comprises a slot through the labial portion of the clip.

11. The self-ligating orthodontic bracket assembly of claim 10 wherein the slot through the labial portion of the clip has a length selected to limit the range of travel of the clip between the open and closed positions.

12. The self-ligating orthodontic bracket assembly of claim 10 wherein the lifting element further comprises a head extending through the slot in the clip.

13. The self-ligating orthodontic bracket assembly of claim 7 wherein the head of the lifting element further comprises a visual indicator of the status of the clip.

14. The self-ligating orthodontic bracket assembly of claim 7 wherein the labial portion of the clip is contoured to follow the contour of the labial surface of the bracket.

* * * * *